United States Patent
Colacello et al.

Patent Number: 5,683,372
Date of Patent: Nov. 4, 1997

[54] MANUAL VENTING AND CUTTING APPARATUS FOR OSTOMY POUCHES

[76] Inventors: Albert A. Colacello, 4 Cranbrook Rd., Hamilton Square, N.J. 08690; Michael A. Colacello, 543 Emmett Ave., Trenton, N.J. 08629

[21] Appl. No.: 636,100

[22] Filed: Apr. 22, 1996

Related U.S. Application Data

[60] Division of Ser. No. 405,005, Mar. 16, 1995, which is a continuation-in-part of Ser. No. 238,884, May 6, 1994, abandoned, which is a division of Ser. No. 100,370, Aug. 2, 1993, Pat. No. 5,372,594.

[51] Int. Cl.$^6$ .................................................. A61F 5/44
[52] U.S. Cl. ........................... 604/333; 604/277; 604/335
[58] Field of Search .................................. 604/332–335, 604/277

[56] References Cited

U.S. PATENT DOCUMENTS

| | | | |
|---|---|---|---|
| 4,863,447 | 9/1989 | Smith | 604/335 |
| 5,372,594 | 12/1994 | Colacello et al. | 604/335 |

*Primary Examiner*—John G. Weiss
*Assistant Examiner*—Dennis Ruhl
*Attorney, Agent, or Firm*—Martin Sachs

[57] ABSTRACT

A manual gas venting and cutting apparatus for use in cutting an opening in and manually venting gas from the interior of a conventional unvented ostomy collection pouch includes a valve assembly having an open position, which permits gas to pass therethrough and a closed position, for preventing gas to pass therethrough. The valve assembly has an input portion for communicating with the interior of the ostomy collection pouch and an output portion for communicating with the atmosphere and a mounting device for mounting the valve assembly to a selected portion of the ostomy collection pouch. The mounting device releasably contains therein a portion of the valve assembly so as to position the input portion thereof proximate the interior of the ostomy collection pouch, and the output portion of the valve assembly proximate to the atmosphere. Also included is a cutting device for providing a geometrically-shaped opening through the ostomy collection pouch, which provides access to the interior thereof utilizing the valve mounting device which, after the opening has been made, is replaced by the valve assembly.

8 Claims, 4 Drawing Sheets

MANUAL VENTING AND CUTTING APPARATUS FOR OSTOMY POUCHES

The present application is a Division of application Ser. No. 08/405,005 filed Mar. 16, 1995 pending; which is a Continuation-in-Part of application Ser. No. 08/238,884, now abandoned filed May 6, 1994, which was a Division of application Ser. No. 08/100,370, now U.S. Pat. No. 5,372,594 filed Aug. 2, 1993, by Albert A. Colacello and Michael A. Colacello.

BACKGROUND OF THE INVENTION

1. Field of the Invention

The present invention relates to venting and cutting apparatuses for ostomy collection pouches and more particularly to a means for cutting an opening in and manually venting ostomy collection pouches into the surrounding atmosphere so that gas build up therein can be released as desired by the wearer thereof.

2. Description of the Prior Art

A colostomy is a surgical procedure in which an artificial anus is formed to accommodate persons whose colon has become infected or cancerous and can no longer function. In such cases the patient is left with no normal bowel function and as a result of the colostomy, body wastes pass through the artificial anus into the colostomy collection bag.

A colostomy can be permanent or temporary but in either event the person must use a pouch system to collect bowel wastes. In some cases after the colon is healed, the surgical procedure is reversed for the temporary colostomy user, normal bowel function follows and the pouch is no longer needed. Unfortunately, permanent colostomy users need a pouch for the rest of their life to handle their body wastes.

Present day colostomy pouches are made of a plastic film. The top portion of the bag includes a hole with an adhesive substance surrounding the hole. This bag is attached to the persons body over the artificial anus and the waste is permitted to enter the pouch through the opening. The bottom part of the pouch may be fitted with a clamp assembly were the waste may be removed while the bag is still attached to the user's body.

Presently available pouches have been designed to serve this purpose well. The waste enters the pouch and is held by the clamp assembly. During use gases from the body and the waste start to build up inside the collection pouch and in most instances there is no way for the gas to be released except through the clamp assembly. This gas build up causes the pouch to blow up and become uncomfortable and very bulky. If the gas situation is not relieved within a reasonable time limit the waste and gas build up can be so great as to pull the pouch away from the body where it is adhered and a uncomfortable situation occurs. As a result, present day pouches and systems limit the mobility of pouch users. They become fearful of moving about because of a perceived embarrassment should a pouch be dislodged.

The desirability of fabricating an ostomy collection pouch with a valve has been recognized in U.S. Pat. No. 4,810,250, issued to Ellenberg, et al. on Mar. 7, 1989, and U.S. Pat. No. 4,863,447, issued to Smith on Sep. 5, 1989. The gas vent of Ellenberg is either fixably secured to the pouch thereof at the time of manufacture or is inserted through a pre-made opening at the time of manufacture or just prior to use by the user. No means are shown or suggested for removing the valve assembly for cleaning. As to the valve assembly disclosed in Smith, such valve assembly is removable from the pouch for cleaning but is taught to cooperate with a special fixture molded into the bag or affixed thereto at the time of manufacture. Another selectively operable vent is shown in U.S. Pat. No. 4,366,836, issued to Villari on Jan. 4, 1983. This vent is also affixed to the ostomy bag at the time of manufacture and may not be readily removed for cleaning.

Vents which cooperate with colostomy bags that are specially manufactured through communicating vents are also shown in U.S. Pat. No. 2,054,535 issued to A. W. Diack on Sep. 15, 1936 and in Offenlegungsschrift 25 57 66 issued to Beiersdorvorf on May 26, 1977. All of the aforementioned venting devices suffer from having to be specially accommodated for in the manufacture of a colostomy bag and additionally in some instances not being readily removable for cleaning, a distinct disadvantage since such valves are likely to foul. Also known in the art are continuously venting gas vent filter assemblies which have the disadvantage of not only having to be manufactured with the ostomy appliances but also suffer from indiscriminate release of gases. Such devices are shown in U.S. Pat. No. 4,203,445 issued to Jessup, et al. on May 20, 1980; U.S. Pat. No. 4,211,224, issued to Kubach, et al. on Jul. 8, 1980; U.S. Pat. No. 4,411,659, issued to Jensen, et al. on Oct. 25, 1983; Offenlegungsschrift DE 3409527 issued to Beiersdorf on Sep. 19, 1985 and Offenlegungsschrift 2,307,063 issued to Virksomheder, et al. on Aug. 23, 1973.

Therefore, a primary object of the present invention is to provide a gas vent assembly for use in manually venting gas from the interior of the conventionally unvented ostomy collection pouch.

A further object of the present invention is to provide a method for installing a gas vent assembly for manually venting gas from the interior of a conventional unvented ostomy collection pouch.

A still further object of the present invention is to provide a gas vent assembly for use in manually venting gas from the interior of a conventional unvented ostomy collection pouch which can be easily and quickly removed from the pouch for cleaning and reinstalled therein without disrupting the use of the pouch.

Still another object of the present invention is to provide a gas vent assembly for use in manually venting gas from the interior of a conventional unvented ostomy collection pouch which can be installed on a conventional unvented ostomy collection pouch by the user.

Still another further object of the present invention is to provide a gas vent assembly for use in manually venting gas from the interior of a conventional unvented ostomy collection pouch which can be moved from the unvented pouch to another unvented pouch venting the same for continuous use.

Another further object of the present invention is to provide a gas vent assembly for ostomy collection pouches which can be selectively vented at any time, by the user and which does not release gas unless the user so desires.

Another further object of the present invention is to provide a vent for ostomy collection pouches which can simply and easily be opened and closed.

An additional object of the present invention is to provide a gas vent assembly for use in venting gas from the interior of a conventional unvented ostomy collection pouch which gives the user much more freedom and mobility then presently known to user's not restricted by travel, work, rest and recreation.

A still additional object of the present invention is to provide a gas vent assembly for use in venting gas from the interior of a conventional unvented ostomy collection pouch so that the pouch does not burst from excess gas.

A still further additional object of the present invention is to provide a gas vent assembly for use in venting gas from the interior of a conventional unvented ostomy collection pouch which provides the user peace of mind and flexibility.

An additional still further object of the present invention is to provide a gas vent assembly for use in venting gas from the interior of a conventional unvented ostomy collection pouch which is simple to design, inexpensive to manufacture, rugged in construction, easy to use, and efficient in operation.

Yet another object of the present invention is to provide a relatively simple, reliable means for providing an opening to the interior of the ostomy pouch.

Yet another object of the present invention is to provide a cutting apparatus that cuts a geometrically-shaped opening in the ostomy collection pouch, provides access to the interior thereof, and which cooperates with the valve mount apparatus.

It is a further object of the present invention to provide a uniform opening in the ostomy bag, which may be readily removed from the internal retainer, which is adapted to removably receive the manually operated valve therein.

These objects as well as further objects and advantages of the present invention will become readily apparent after reading the ensuing description of a non-limiting illustrative embodiment and reviewing the accompanying drawing.

SUMMARY OF THE INVENTION

A manually operable gas venting and cutting assembly for use in providing an opening for venting gas from the interior of a conventional unvented ostomy collection pouch, constructed in accordance with the principles of the present invention, includes a manually operable valve assembly having an open position, which permits gas to pass therethrough and a closed position for preventing gas from passing therethrough. The valve assembly has an input portion for communicating with the interior of the ostomy collection pouch and an output portion for communicating with the atmosphere, and a mounting device for mounting the valve assembly through a selected portion of the ostomy collection pouch. The ostomy collection pouch is essentially uniform prior to the mounting of the valve assembly. The mounting device for releasably retaining therein a portion of the valve assembly positions the input portion of the valve assembly proximate the stoma of the wearer. The mounting device for releasably retaining therein a portion of the valve assembly is disposed within the interior of the collection pouch.

A cutting means, for cutting a geometrically-shaped opening through the ostomy collection pouch for providing access to the interior thereof, and for permitting the insertion of the valve assembly therethrough, is utilized together with the internal retainer in order to cut the opening in the pouch, and thereafter is removed and replaced with the manually operable valve assembly.

A method for providing a manually operable venting means for an ostomy collection pouch in accordance with the principles of the present invention, includes the steps of: providing a valve assembly; providing means for removably retaining said valve assembly; providing cutting means for cutting a geometrically-shaped hole through to the interior of said ostomy collection pouch utilizing the means for removably retaining the valve assembly; inserting the valve assembly through the hole; and removably affixing the manually operable valve assembly within said removable retaining means.

BRIEF DESCRIPTION OF THE DRAWINGS

In order that the present invention may be more fully understood, it will now be described, by way of example, with reference to the accompanying drawing, in which.

DESCRIPTION OF THE PREFERRED EMBODIMENT

Figure 1:
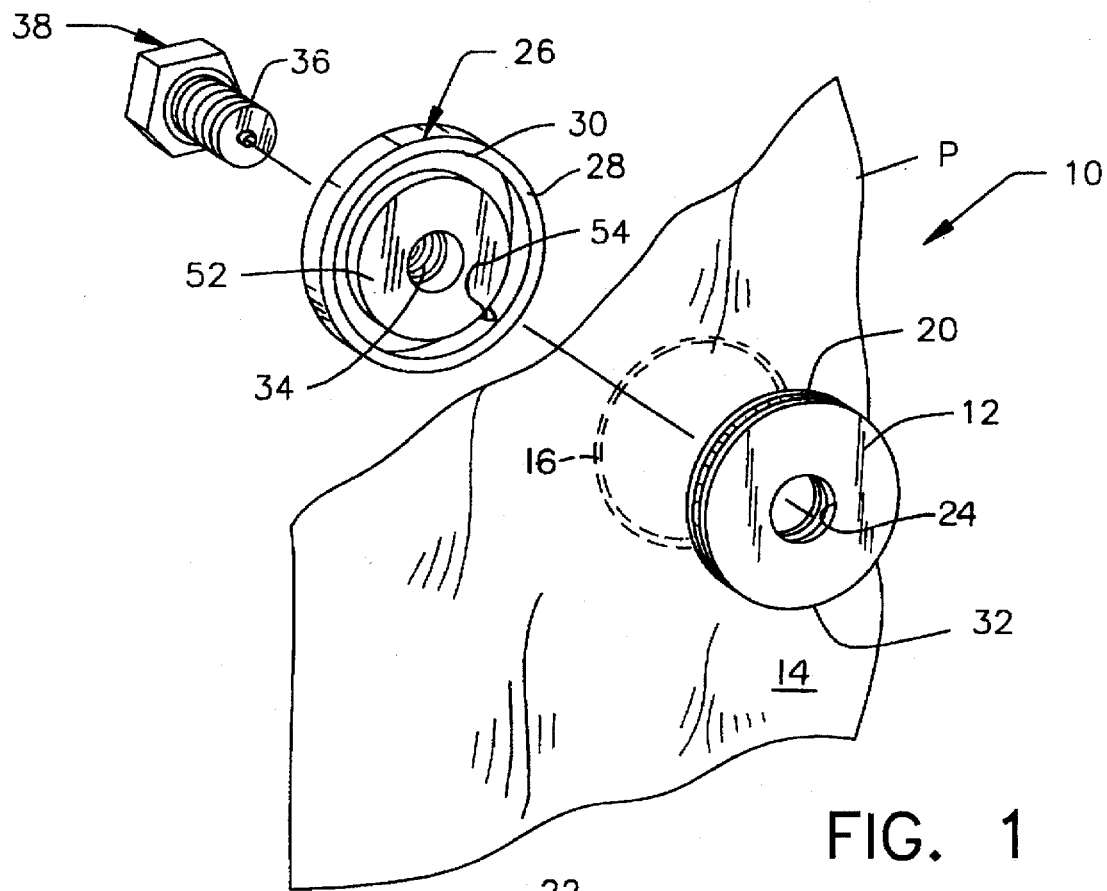
FIG. 1 is a pictorial representation of an ostomy collection pouch, incorporating the principles of the present invention, prior to mounting over a patient's stoma, showing the interior of the ostomy pouch, showing the internal retainer member disposed on the interior thereof, with the cutting apparatus disposed on the exterior thereof.
Figure 2:
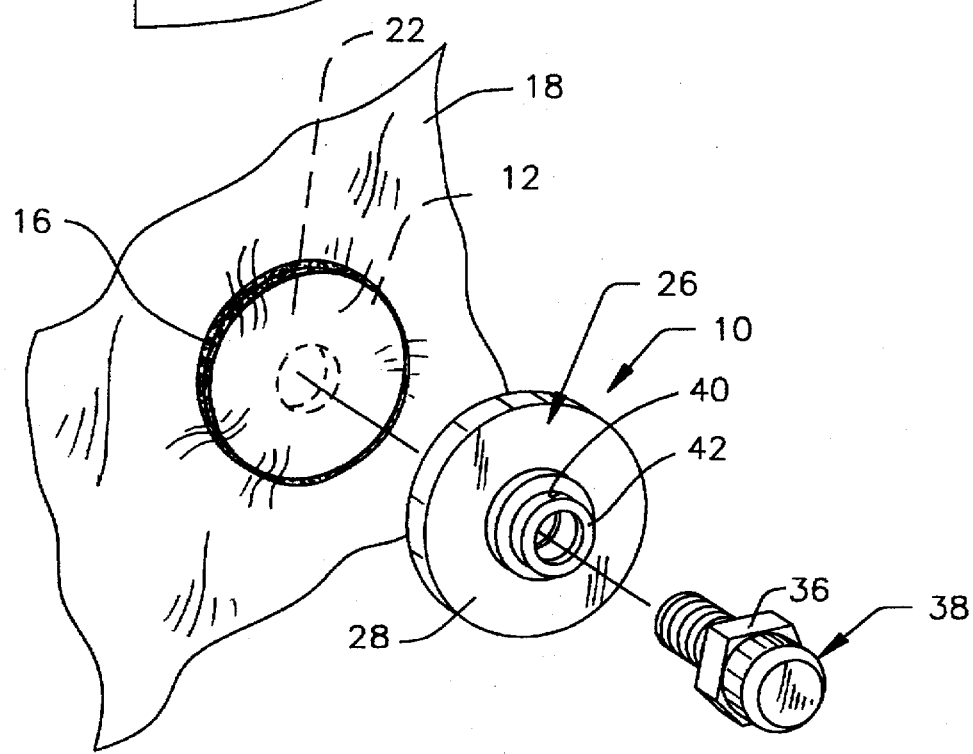
FIG. 2 is a pictorial representation of an ostomy collection pouch after the internal retainer has been affixed to the interior of the pouch and the cutting mechanism being applied thereto.

Referring now to the figures, and more particularly, to FIGS. 1 and 2, there is illustrated a portion of a conventional ostomy collection pouch (P), which has an essentially uniform wall thickness, viewed from the inside thereof. The ostomy pouch is of a conventional unvented design, and is to have mounted thereto a manual gas venting and cutting assembly, as will be explained in detail hereinafter. The pouch (P) is of a conventional unvented design, and will be prepared for use in accordance with the principles of the present invention. An internal retainer 12 is inserted through the opening, not shown, of a conventional ostomy pouch (P), of which only a portion is shown in FIGS. 1 and 2. Once the internal retainer is inserted into the ostomy pouch (P), it is placed in a convenient area against the inner surface 14 of the pouch (P) and retained in position along the inner wall surface 14 by an O-ring 16 placed over the outer wall 18 of the pouch (P). The O-ring 16 is disposed within a groove or channel 20 circumscribing the circumference of the internal retainer 12. Thus, the O-ring 16 stretches the outer or external surface 18 of the pouch (P), holding the pouch (P) in a taut position against the surface 22 thereof. The internal retainer 12 is provided with a centrally disposed threaded aperture 24, whose function will be described hereinafter.

A cutting assembly 26 includes a cooperating disc 28, which is provided with an inside diameter 30, which is adapted to cooperate with the external diameter of the internal retainer 12 plus the thickness of a portion of the ostomy pouch (P) disposed therearound. The internal retainer is also provided with a centrally disposed through hole or aperture 34, which is adapted to cooperate with and receive the input portion 36 of a valve assembly 38 (see FIG. 3), which will be described in detail hereinafter. The cooperating disc 28 of the cutting assembly 26 is provided with a centrally disposed aperture or opening, which is adapted to receive the elongated holding device 42, which is threaded on one end portion 44 with mating threads adapted to receive the input portion 36 of the valve assembly 38 and stop at the remaining unthreaded portion 43, the shoulder 46 provided within the threaded portion 44 of the aperture 40.

The elongated holding device 42 is held in position and remains rotatively affixed to the cooperating disc 28 by means of a locking ring 48 placed over one end 50 of the elongated holding device 42, thus allowing for free rotation of the elongated holding device. The other end 52 has provided thereon a cutting device 54, which may be a sharp edge or burr, and it is disposed in a position where it will form a geometrically-shaped path when rotated as shown by arrow 55 so that it will cut out a portion 56 of the ostomy collection pouch (P) the size of the internally threaded aperture 24 of the internal retainer (see FIG. 3).

Figure 3:
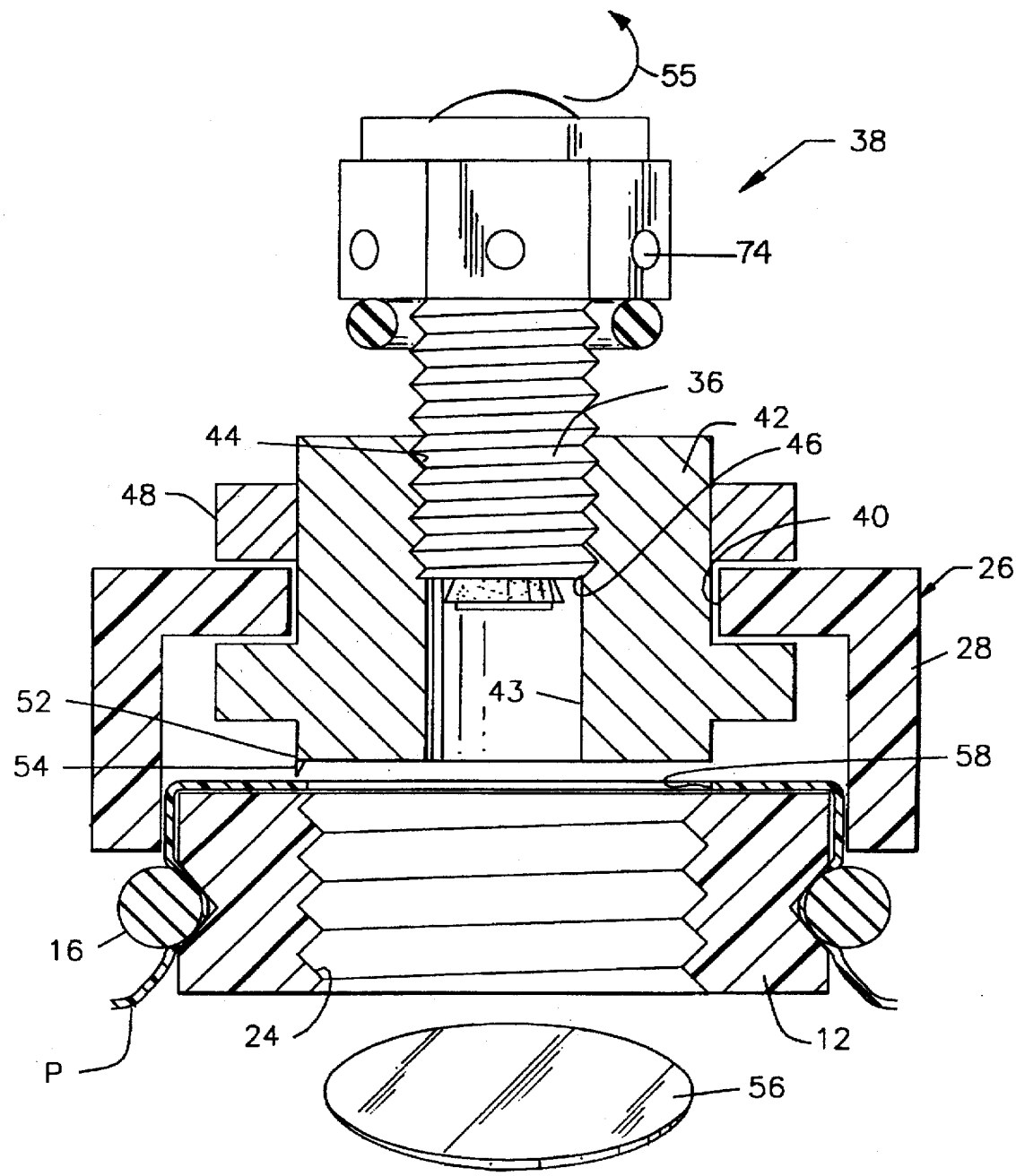
FIG. 3 is an enlarged cross-sectional view in elevation showing the geometrically-shaped opening provided to the interior of the ostomy collection pouch.

FIG. 3 is a partial cross-sectional view in elevation of the cutting assembly 26 positioned over the internal retainer and the ostomy pouch (P) just after a geometrically-shaped opening has been provided in the ostomy collection pouch (P) by removing a portion 56 therefrom. The rotation of the elongated holding device 42 as shown by arrow 55 by the valve assembly 38 causes the cutting device 54 to severe the pouch in a uniform, reliable manner.

Figure 4:
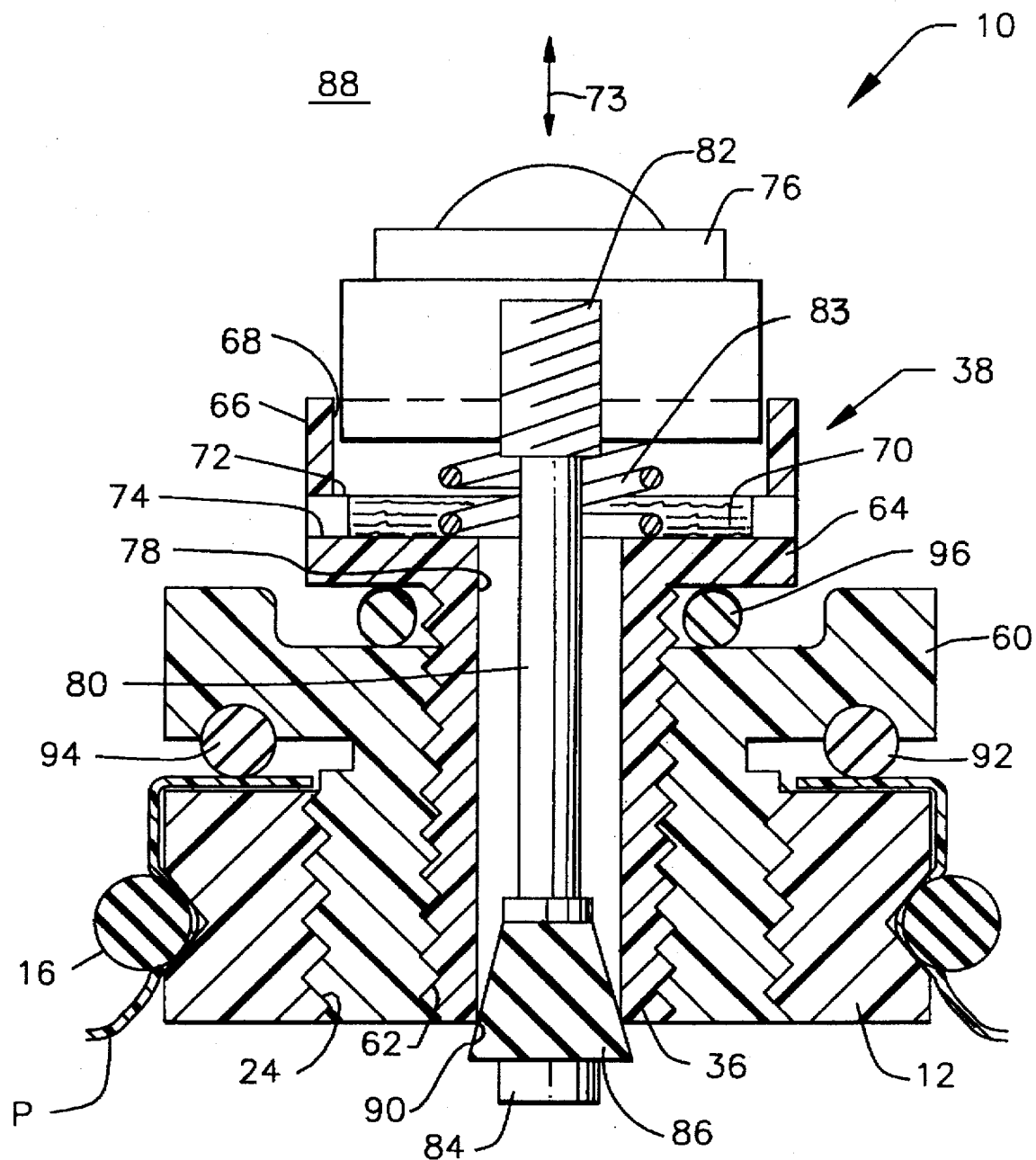
FIG. 4 is a an enlarged cross-sectional view in elevation of the valve assembly being assembled with the internal retainer with the valve in the closed position.
Figure 4A:
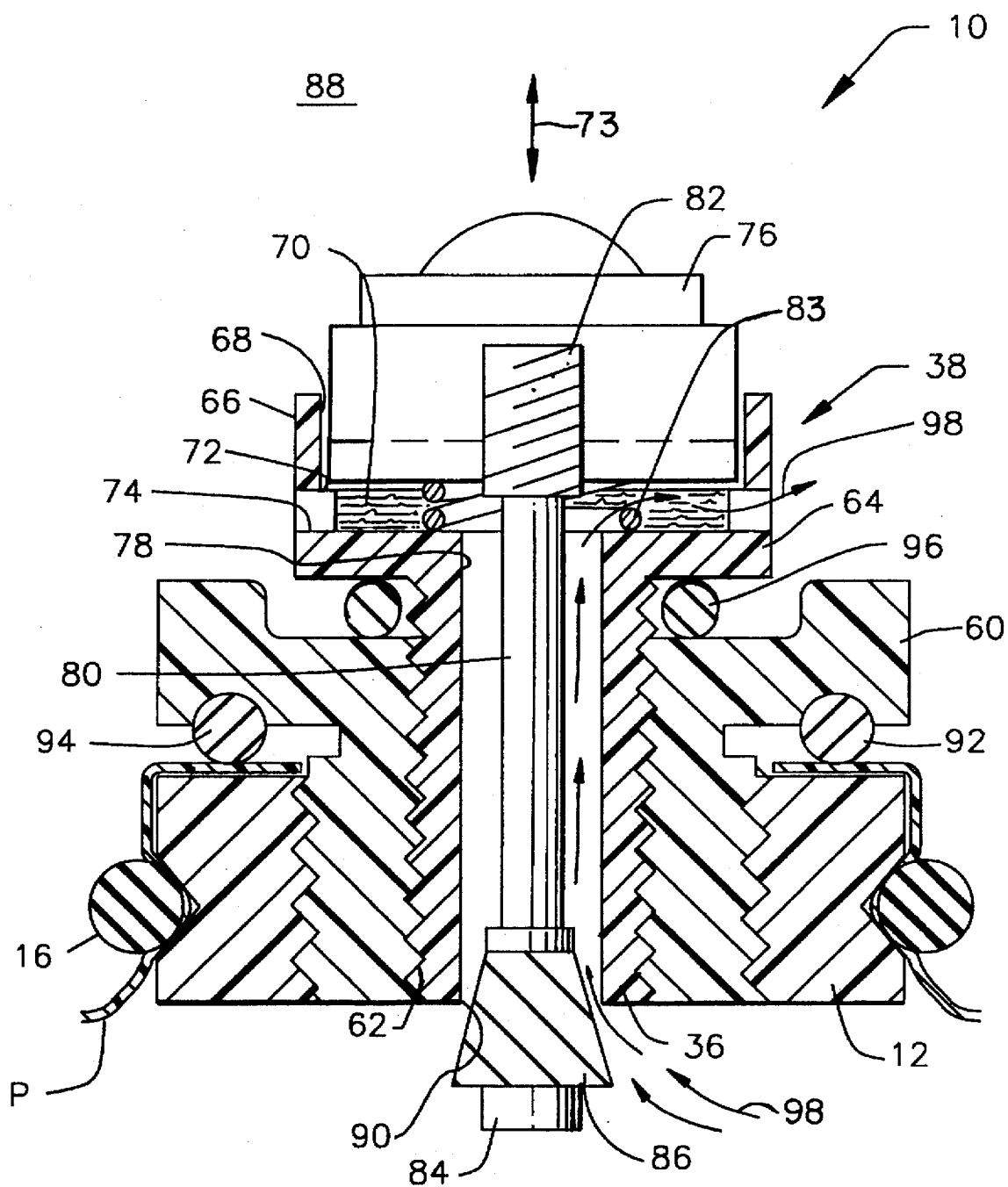
FIG. 4A is an enlarged cross-sectional view in elevation of the assembly shown in FIG. 4, with the valve in its open or venting position, allowing gases from the interior of the ostomy pouch to escape therefrom.

Referring now to FIGS. 4 and 4A, there is shown a valve assembly 38, which includes an input or invasive portion 36, which is threaded on one end, which is adapted to be received into a mounting 60. The mounting 60 is provided with a centrally disposed threaded through aperture 62 adapted to cooperate and receive the threaded portion 36 of the valve assembly 38. The other end 64 of the valve assembly 38 is provided with an enlarged head in which is provided a reservoir 68 that is adapted to receive an absorbent pad 70 into which may be placed an antiseptic and/or deodorant and has a valve stop 72 disposed therein. Around the circumference below the valve stop 72 there is provided a plurality of through apertures 74, the function of which will be described hereinafter.

The valve stop 72 is dimensioned to cooperate with a valve head 76 which is moved as shown by arrow 73 and, when in contact with the valve stop 72, allows for the passage of gas through the longitudinal bore 78 provided in the input portion 36 of the valve assembly 38 as shown by the arrows 98. The valve head 76 is threaded on a valve stem 80 at one end 82 and is biased in an open position away from the valve stop 72 by a spring 83. The other end 84 of the valve stem 80 has affixed thereon, in a conventional manner, a tapered rubber stopper 86 so that when it comes into contact with the opening of the longitudinal bore 78, it cuts off and seals the interior of the ostomy collection pouch (P) from the outside atmosphere 88. Therefore, by pressing on the valve head 76 in the direction of arrow 73, the stopper 86 will be removed from contact with the edge 90 of the longitudinal bore 78 provided in the input or invasive portion 36 of the valve assembly 38. An O-ring 92 is disposed in a groove 94 provided on the underside of the mounting 60 so that when the mounting 60 is threaded into the internal retainer 12, the pouch (P) is sealed proximate the circumference of the opening 58 to prevent the leakage of gases or any effluent disposed within the pouch (P), thereby providing a double seal for the manual gas venting assembly 10 when affixed to the pouch (P). Another O-ring 96 is disposed beneath the other end of the enlarged head 66 so that when the valve head is threaded into the mounting 60, an additional seal is made so that gases attempting to escape from the pouch (P) along the threads 62 will be prevented from entering the atmosphere.

Referring now to FIG. 4A, which is a cross sectional view of the valve assembly shown in FIG. 4, except that it shows the operation with the valve-being manually depressed so that the gases disposed within the interior of the pouch (P) will follow the path shown by arrows 98 until it exits, via the apertures 74 provided in the enlarged head 66 of the valve assembly 38. In doing so, the gases will pass through the absorbent pad 70, which may contain an antiseptic and/or deodorant.

In operation, the internal retainer is inserted through the discharge opening, not shown, of an ostomy collection pouch and is held in position until an O-ring 16 is placed thereover from the external surface of the pouch (P), thereby holding the pouch (P) tautly over the internal retainer. The cooperating disc 28 of the cutting assembly 26 is placed over the internal retainer from the outside or exterior of pouch (P). The input or invasive portion 36 of valve assembly 38 is threaded into aperture 34 provided in the cooperating disc 28 so that the other end 52 of the elongated holding device and the cutting device 54 comes into contact with the exterior surface of the pouch (P). Rotation of the valve assembly will rotate the cutting device so that a geometrically-shaped (circular) opening is cut into the pouch (P). The valve assembly 38 is removed from the cutting assembly 26 and the cutting assembly is removed from the internal retainer 12. The valve assembly 38 is then threaded into the mounting 60, using the O-ring 96 therebetween to make a good seal. The mounting 60, with the valve assembly 38 disposed therein, is then threaded into the cooperating threaded aperture 24 provided in the internal retainer 12, thereby completing the assembly. It is to be noted that the valve assembly may be removed at any time from the mounting 60 so that it may be washed, cleansed, or antiseptic medicament may be added to the valve assembly 38 as required.

It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what is claimed is:

1. A method of providing a manually operable venting means for an ostomy collection pouch comprising the steps of:
   A. providing an ostomy collection pouch having an interior;
   B. providing a valve assembly;
   C. providing means for removably retaining said valve assembly disposed within said interior of said pouch;
   D. providing cutting means and cutting a geometrically-shaped opening through said ostomy collection pouch to said interior of said ostomy collection pouch utilizing said cutting means and said means for removably retaining said valve assembly;

E. removing said cutting means from said means for removably retaining said valve assembly;

F. inserting said valve assembly through said geometrically-shaped opening; and

G. removably affixing said manually operable valve assembly within said removable retaining means.

2. The method of providing a manually operable venting means for an ostomy collection pouch according to claim 1 wherein said valve assembly is normally closed and manually operable to permit the ostomy collection pouch to vent into the atmosphere.

3. The method of providing a manually operable venting means for an ostomy collection pouch according to claim 1, wherein said valve assembly is threaded into said removable retaining means.

4. The method of providing a manually operable venting means for an ostomy collection pouch according to claim 1, wherein said valve assembly may be readily disassembled for cleaning.

5. A method of providing a manual venting means for an ostomy collection pouch comprising the steps of:

A. providing an ostomy collection pouch having an interior;

B. providing a combined manually operable valve assembly and piercing means for cutting an opening in said ostomy collection pouch;

C. providing means for removably retaining said combined manually operable valve assembly and piercing means disposed within said interior of said pouch;

D. creating an opening through said ostomy collection pouch to said interior of said ostomy collection pouch by utilizing said piercing means;

E. inserting a portion of said combined manually operable valve assembly and piercing means through said opening; and F. removably affixing said combined manually operable valve assembly and piercing means within said removable retaining means.

6. The method of providing a manually operable venting means for an ostomy collection pouch according to claim 5 wherein said combined manually operable valve assembly and piercing means is normally closed and manually operable to permit the ostomy collection pouch to vent into the atmosphere.

7. The method of providing a manually operable venting means for an ostomy collection pouch according to claim 5, wherein said combined manually operable valve assembly and piercing means is threaded into said removable retaining means.

8. The method of providing a manually operable venting means for an ostomy collection pouch according to claim 5, wherein said combined manually operable valve assembly and piercing means may be readily disassembled for cleaning.

* * * * *